United States Patent
Hahn

(10) Patent No.: US 8,319,964 B2
(45) Date of Patent: Nov. 27, 2012

(54) METHOD AND APPARATUS TO LASER ABLATION—LASER INDUCED BREAKDOWN SPECTROSCOPY

(75) Inventor: David Worthington Hahn, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/382,825

(22) PCT Filed: Jul. 12, 2010

(86) PCT No.: PCT/US2010/041705
§ 371 (c)(1),
(2), (4) Date: Jan. 6, 2012

(87) PCT Pub. No.: WO2011/006156
PCT Pub. Date: Jan. 13, 2011

(65) Prior Publication Data
US 2012/0099103 A1  Apr. 26, 2012

Related U.S. Application Data

(60) Provisional application No. 61/224,506, filed on Jul. 10, 2009.

(51) Int. Cl.
*G01J 3/30* (2006.01)
(52) U.S. Cl. .................................................. 356/318
(58) Field of Classification Search ............... 356/318
See application file for complete search history.

(56) References Cited

U.S. PATENT DOCUMENTS

| | | | |
|---|---|---|---|
| 5,889,587 | A | 3/1999 | D'Silva et al. |
| 6,002,478 | A | 12/1999 | Zhu |
| 6,008,897 | A | 12/1999 | Sabsabi et al. |
| 6,532,068 | B2 | 3/2003 | Detalle et al. |
| 6,661,511 | B2 | 12/2003 | Detalle et al. |
| 2009/0290151 | A1* | 11/2009 | Agrawal et al. ............ 356/318 |

FOREIGN PATENT DOCUMENTS

JP  2009-110853  5/2009

OTHER PUBLICATIONS

Arrowsmith et al., "Entrainment and Transport of Laser Ablated Plumes for Subsequent Elemental Analysis", 1988 Applied Spectroscopy, vol. 42, No. 7, 1231-1239.*

(Continued)

*Primary Examiner* — Kara E Geisel
(74) *Attorney, Agent, or Firm* — Saliwanchik, Lloyd & Eisenschenk

(57) ABSTRACT

A method and apparatus for analyzing a target material is provided. A first laser beam pulse can be incident on a target material to create an ablation event so as to produce an ablation plume of target material. Such ablation events can include plasma ablation, sub-plasma ablation, and thermal desorption. At least a portion of the ablation plume of target material can then be transported a sufficient distance away from the ablation event that a second laser beam pulse can interact with the at least a portion of the ablation plume of target material to create an analytical plasma such that the analytical plasma is uncoupled from the ablation event. The creation of the analytical plasma results in one or more elements of the at least a portion of the ablation plume of target material undergoing atomic emission, which can be collected and analyzed.

40 Claims, 12 Drawing Sheets

OTHER PUBLICATIONS

Bulajic, D., et al., "A Procedure for Correcting Self-Absorption in Calibration Free-Laser Induced Breakdown Spectroscopy," *Spectrochimica Acta Part B: Atomic Spectroscopy*, Feb. 2002, vol. 57, No. 2, pp. 339-353.

Carranza, J.E., et al., "Assessment of the Upper Particle Size Limit for Quantitative Analysis of Aerosols Using Laser-Induced Breakdown Spectroscopy," *Analytical Chemistry*, Nov. 2002, vol. 74, No. 21, pp. 5450-5454.

Fisher, B.T., "Temporal Gating for the Optimization of Laser-Induced Breakdown Spectroscopy Detection and Analysis of Toxic Metals," *Applied Spectroscopy*, Oct. 2001, vol. 55, No. 10, pp. 1312-1319.

Vors, E., "Laser-Induced Breakdown Spectroscopy (LIBS) for Carbon Single Shot Analysis of Micrometer-Sized Particles," *Analytical and Bioanalytical Chemistry*, Jun. 2006, vol. 385, No. 2, pp. 281-286.

Windom, B.C., et al., "Laser Ablation—Laser Induced Breakdown Spectroscopy (LA-LIBS): A Means for Overcoming Matrix Effects Leading to Improved Analyte Response," *Journal of Analytical Atomic Spectrometry*, 2009, vol. 24, No. 12, pp. 1665-1675.

* cited by examiner

METHOD AND APPARATUS TO LASER ABLATION—LASER INDUCED BREAKDOWN SPECTROSCOPY

CROSS-REFERENCE TO RELATED APPLICATIONS

The present application is the U.S. National Stage Application of International Patent Application No, PCT/US2010/041705, filed on Jul. 12, 2010, which claims the benefit of U.S. Provisional Application Ser. No. 61/224,506, filed Jul. 10, 2009, both of which are hereby incorporated by reference herein in their entirety, including any figures, tables, or drawings.

STATEMENT REGARDING FEDERALLY SPONSORED RESEARCH OR DEVELOPMENT

The subject invention was made with government support under a research project supported by National Science Foundation, Contract No. CHE-0822469. The government has certain rights to this invention.

BACKGROUND OF INVENTION

A fundamental problem with real time quantitative chemical analysis under the current state of technology is the non-linear analyte response that may occur when the composition of a sample's background matrix is altered. The inconsistencies that occur when investigating an analyte in different material matrices are generally referred to as matrix effects. For true quantitative analysis, calibration of the analytical tool is typically made with matrix matched samples, presenting limitations in performing in situ and real time analysis, and adding cost and complexity Inductively-coupled plasma—atomic emission spectroscopy (ICP-AES) is a long-established analytical technique for elemental analysis. An induction coil is used to create a steady-state plasma. Materials to be analyzed (referred to as the analyte) are digested in acids, and then introduced into the ICP via a nebulizer. The nebulizer makes small droplets containing the acid solution and dissolved analyte species, which then flow into the hot plasma (T~6,000-10,000 K), where the droplets are vaporized and the analyte species are dissociated to atoms and ions. The atoms and ions are excited within the hot plasma, resulting in atomic emission. The atomic emission is collected and analyzed (i.e., atomic emission spectroscopy), which forms the basis of ICP-AES as an analytical scheme. Typically, calibration solutions are also analyzed, enabling quantification of the analyte signal by direct comparison of atomic emission intensity. ICP-AES enjoys high sensitivity, but drawbacks include the relatively high equipment costs and the need for sample preparation (i.e. digestion).

Inductively-coupled plasma—mass spectrometry (ICP-MS) is widely viewed as an improvement to ICP-AES. Basically, with ICP-MS, all the above steps of ICP-AES are followed. However, at the exit of the inductively-coupled plasma, there is an inlet to a mass spectrometer (MS). Hence some atoms and ions are swept into the mass spectrometer instrumentation, where the mass/charge ratio is measured and quantified. With ICP-MS, the steps of digestion and nebulization, and then vaporization and dissociation to atoms and ions, are used to introduce the appropriate form of analyte (namely ions) into the mass spectrometer. Advantages of MS as the actual sensor, rather than AES, include increased sensitivity, as well as elimination of some optical interference that can occur with AES. Drawbacks of ICP-MS include relatively higher equipment costs and complexity as compared to ICP-AES, and the required sample preparation (i.e., digestion).

Laser ablation ICP-AES (LA-ICP-AES) and laser ablation ICP-MS (LA-ICP-MS) use a laser to ablate the sample. With laser-ablation, the analyte sample is placed in an ablation cell (small vessel with optical access via windows), and a pulsed laser beam is used to ablate a portion of the sample. The ablation plume (atoms, ions and small particles) is then passed into the ICP using a carrier gas, where all processes are as described above. In essence, the digestion and nebulization step is replaced with direct laser sampling via laser ablation. The advantages of LA are the elimination of time-consuming sample digestion, and the ability for micro-analysis and spatial mapping. The drawbacks include additional cost and complexity, as well as the potential for introduction of matrix effects during the laser ablation step. Matrix effects in general refer to conditions where the actual analyte signal depends on the material matrix from which the element in question originated. Ideally, the analyte signal (e.g., AES signal or MS signal) only depends on the quantity of the particular element of interest. If the analyte signal is influenced by the presence of other elements, that is a matrix effect. Matrix effects can originate in the ICP step. However, the laser ablation step can introduce additional matrix effects due to things like (1) non-stoichiometric ablation, in which the ablation plume elemental concentrations do not match the elemental concentrations of the original solid material, and (2) non-stoichiometric transport, in which the elements in the ablation plume are not transported equally to the ICP and/or to the MS.

Laser-induced breakdown spectroscopy (LIBS) is considered an analytical spectroscopy technique in which a pulsed laser beam is used to create a laser-induced plasma. The laser induced plasma can be formed in gases, in aerosols (mixtures of gas and suspended particles), on and in liquids, and directly on solid surfaces. The laser-induced plasma is characterized by temperatures of 10,000 to 40,000 K and is highly ionized. The laser-induced plasma serves two functions with the LIBS technique. First, the laser-induced plasma samples the analyte by vaporizing and dissociating the analyte species to atoms and ions. Second, the laser-induced plasma then excites the atoms and ions, and the resulting atomic emission is collected and analyzed. The elimination of sample preparation allowing rapid and direct analysis is generally extolled as an advantage of LIBS. The primary disadvantage of LIBS is the lack of precision and sensitivity as compared to other analytical schemes. The large background emission (continuum radiation) of the hot laser-induced plasmas can mask and reduce the signal-to-noise ratios of the atomic emission signal from the analyte species, resulting in a lack of sensitivity. A lack of precision can be considered to arise from the highly non-linear laser-material interactions that occur during plasma formation and analyte vaporization. The plasma formation and growth can be highly related to the laser-material interactions; hence, the resulting plasmas can show considerable variation in the temporal and spatial development, and in the temporal and spatial temperature and free electron density profiles. These items can directly affect the analyte sampling, vaporization, dissociation, and ionization processes, which then all affect the atomic emission signal. Because the laser beam functions as both the sampling laser and to create the analytical plasma, elimination of these effects is difficult if not possible.

An application of LIBS is the direct analysis of solid materials. This application takes advantage of LIBS to eliminate the need for sample preparation (e.g., digestion). However, due to the laser-sample coupling, matrix effects are generally present. Additional effects can result from the interference of the atmosphere above the sample. As the laser beam strikes the solid sample and begins to form the plasma, the growing plasma as well as the remaining laser pulse may interact with the atmosphere above the sample. In some cases, the gas above the surface can absorb considerable laser energy, thereby obscuring the targeted material. Such problems can lead to additional non-linearities and loss of analytical precision and accuracy. To help mitigate such problems, a dual-pulse LIBS methodology has been implicated. With dual-pulse LIBS, two laser beams are used, typically separated in time by nanoseconds to tens of microseconds. There are many arrangements, including having the two lasers either parallel to each other or orthogonal to each other. On advantage of dual-pulse LIBS is that the initial laser-induced plasma formed by the first laser can rarify the atmospheric gas above the sample surface, thereby allowing the second laser to couple better into the target (i.e., laser-surface coupling) rather than couple into the cover gas (i.e., laser-atmosphere coupling or plasma-shielding). This can increase the mass of analyte sampled. Another benefit associated with dual-pulse LIBS is increased sensitivity. For example, the second pulse can "re-heat" the plasma, or as noted above, better couple into the solid material, with the ultimate benefit of increased analyte signal response.

BRIEF SUMMARY

Embodiments of the invention relate to a method and apparatus for analyzing a target material. Specific embodiments can be referred to as laser ablation laser-induced breakdown spectroscopy (LA-LIBS). Embodiments of the invention relate to the use of a first laser beam pulse incident on a target material to create an ablation event so as to produce an ablation plume of target material. Such ablation events can include, for example, plasma ablation, sub-plasma ablation, and thermal desorption. At least a portion of the ablation plume of target material can then be transported a sufficient distance away from the ablation event that a second laser beam pulse can interact with the at least a portion of the ablation plume of target material to create an analytical plasma such that the analytical plasma is uncoupled from the ablation event. The creation of the analytical plasma results in one or more elements of the at least a portion of the ablation plume of target material undergoing atomic emission, which can, optionally, be collected and analyzed. Referring to FIG. 1, a specific embodiment, the embodiment describes the use of separate laser-induced plasmas. The first plasma, referred to as the ablation plasma, is used to ablate target material, thereby introducing target material (vapor and fine particles) into the carrier gas stream. The carrier gas stream then transports the ablated material into the second region, a laser-induced plasma, referred to as the analytical LIBS plasma, where the elements are vaporized and undergo atomic emission. The emission from the analytical LIBS plasma is then collected and analyzed. The two lasers can be synchronized using the delay controller. For a combination of carrier gas flow rate and inter-laser delay time, an optimal setting may be realized such that the bulk of ablation plume from the ablation plasma is transported and centered within the analytical LIBS plasma. Referring to FIG. 2, a specific embodiment is described making use of a single laser and beam splitter to achieve the laser ablation and analytical current single-laser and double-laser LIBS because the ablation plasma and the analytical plasma can be completely uncoupled. When the ablation event, such as an ablation plasma, and the analytical plasma are uncoupled, non-linearities in the plasma breakdown and analyte responses due to laser-material, plasma-material, laser-plasma, plasma-plasma, and laser-laser coupling can be reduced or eliminated.

for the SM-10 reference material. The spectra have been shifted for clarity and do not have the same intensity scale in accordance with embodiments of the subject invention.

Figure 10:
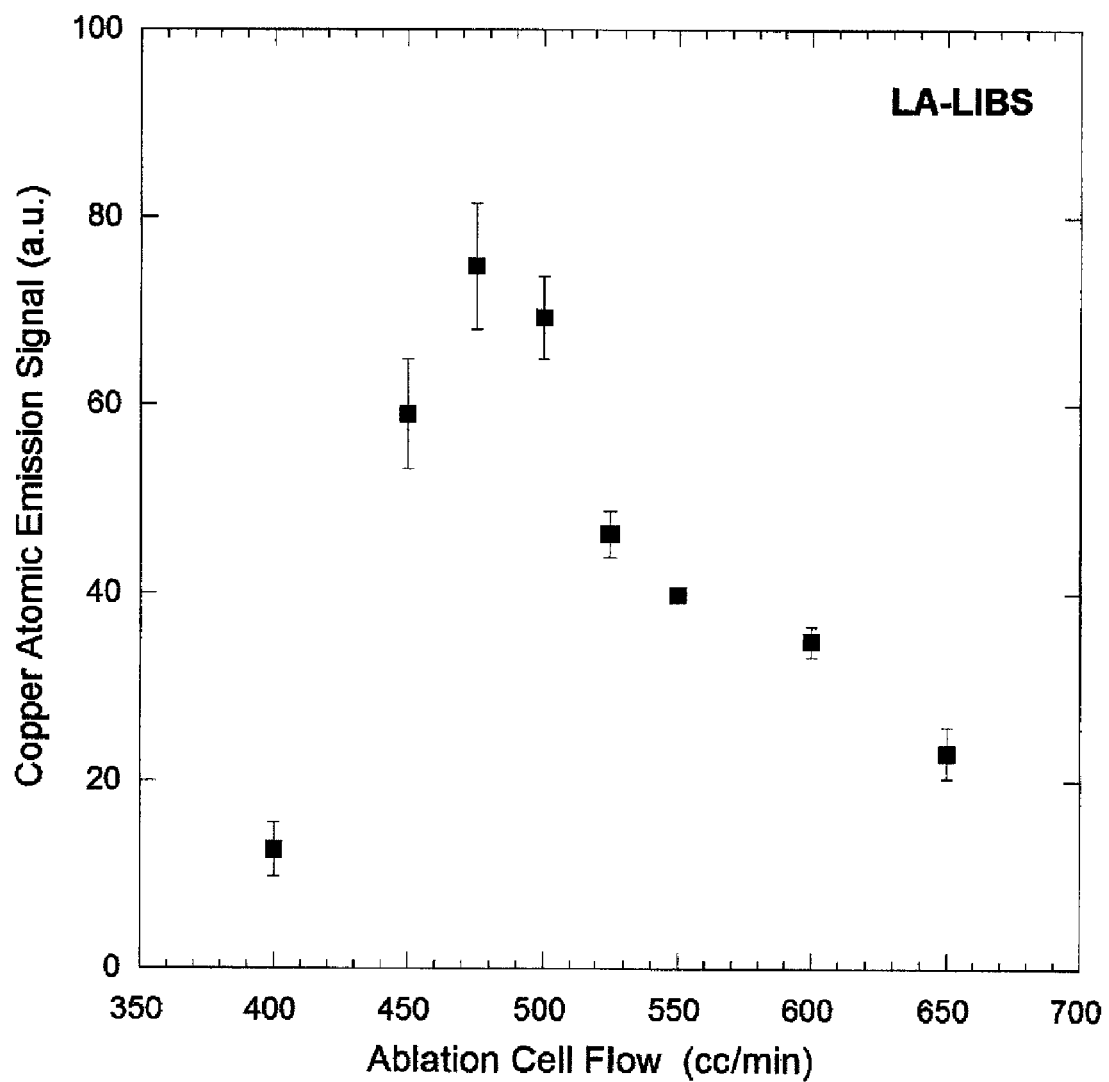

FIG. 10 shows the copper atomic emission signal as a function of the carrier gas flow rate for a specific embodiment of the invention.

DETAILED DISCLOSURE

Figure 1:
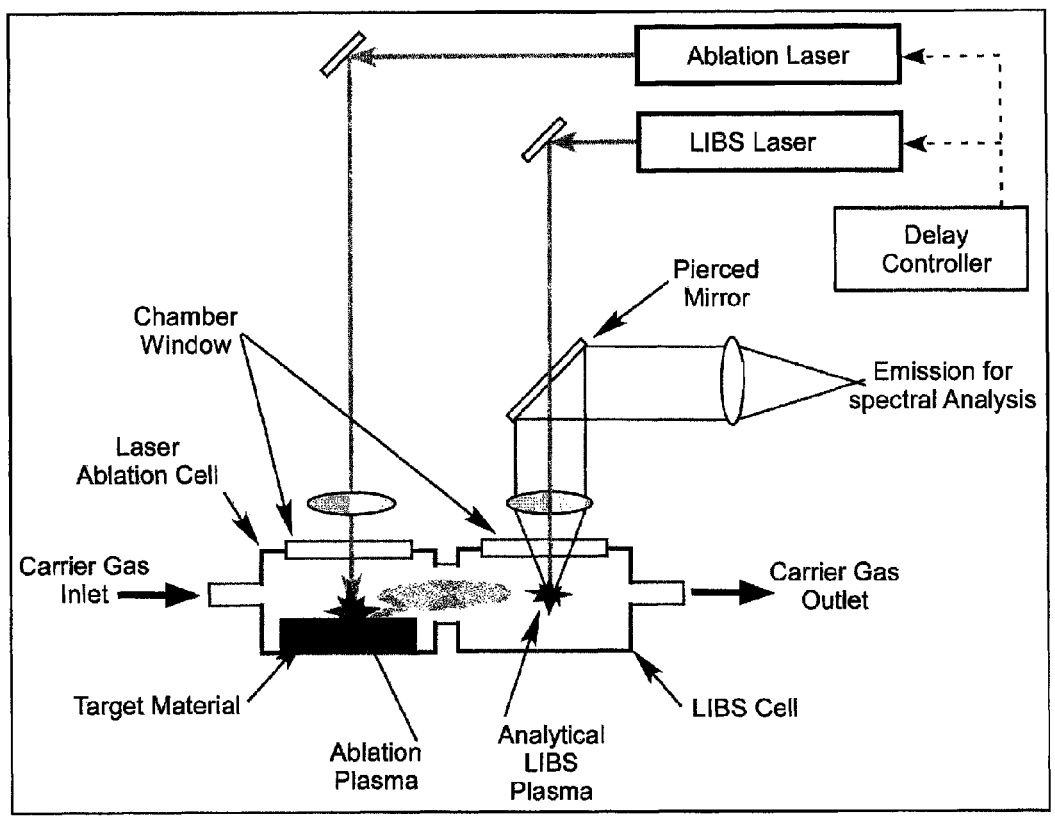
FIG. 1 shows an embodiment of an apparatus for elemental analysis in accordance with an embodiment of the subject invention.
Figure 2:
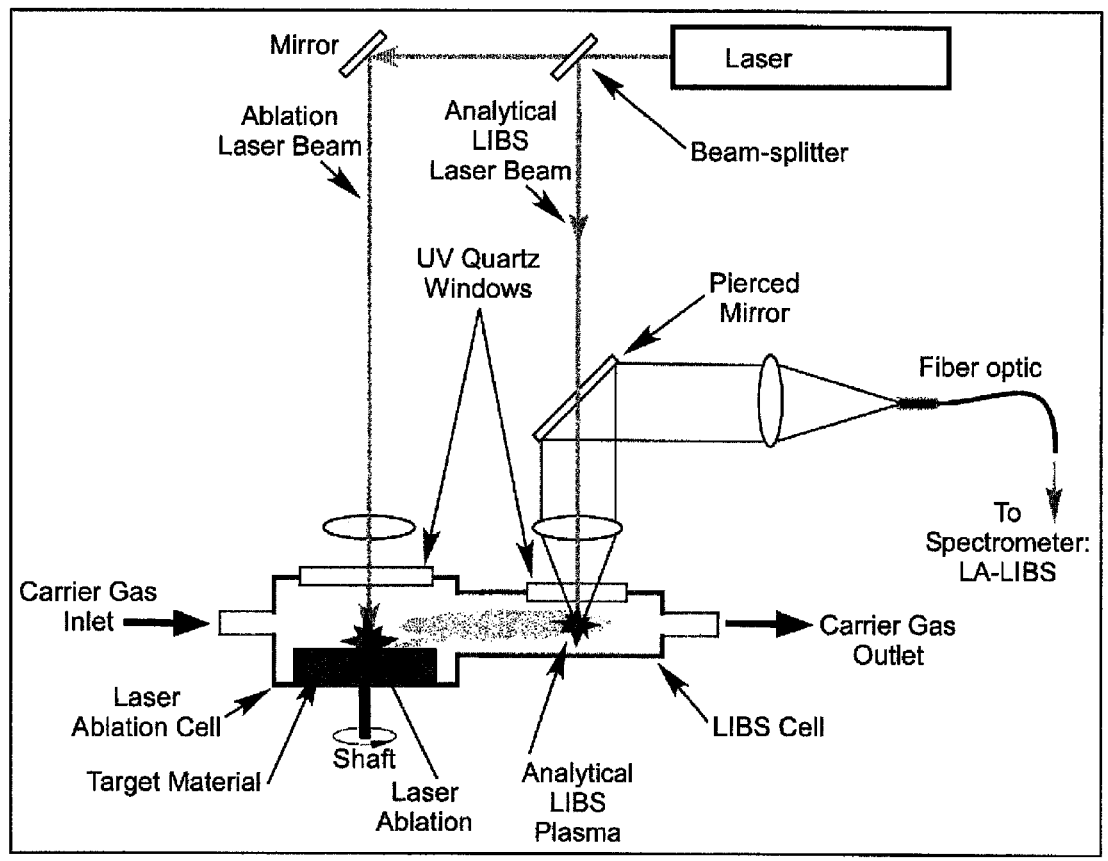
FIG. 2 shows an experimental configuration depicting the LA-LIBS scheme using a single Laser and beam-splitter, resulting in a laser beam for laser ablation, and a laser beam for generation of the analytical LIBS plasma in accordance with an embodiment of the subject invention.

Embodiments of the invention relate to a method and apparatus for analyzing a target. Specific embodiments can be referred to as laser ablation laser-induced breakdown spectroscopy (LA-LIBS). Embodiments of the invention relate to the use of a first laser beam pulse incident on a target material to create an ablation event so as to produce an ablation plume of target material. Such ablation events can include, for example, plasma ablation, sub-plasma ablation, and thermal desorption. At least a portion of the ablation plume of target material can then be transported a sufficient distance away from the ablation event that a second laser beam pulse can interact with the at least a portion of the ablation plume of target material to create an analytical plasma such that the analytical plasma is uncoupled from the ablation event. The creation of the analytical plasma results in one or more elements of the at least a portion of the ablation plume of target material undergoing atomic emission, which can, optionally, be collected and analyzed. Referring to FIG. 1, a specific embodiment, the embodiment describes the use of separate laser-induced plasmas. The first plasma, referred to as the ablation plasma, is used to ablate target material, thereby introducing target material (vapor and fine particles) into the carrier gas stream. The carrier gas stream then transports the ablated material into the second region, a laser-induced plasma, referred to as the analytical LIBS plasma, where the elements are vaporized and undergo atomic emission. The emission from the analytical LIBS plasma is then collected and analyzed. The two lasers can be synchronized using the delay controller. For a combination of carrier gas flow rate and inter-laser delay time, an optimal setting may be realized such that the bulk of ablation plume from the ablation plasma is transported and centered within the analytical LIBS plasma. Embodiments of the subject method can offer significant advantages over current single-laser and double-laser LIBS because the ablation plasma and the analytical plasma can be completely uncoupled. When the ablation event, such as an ablation plasma, and the analytical plasma are uncoupled, non-linearities in the plasma breakdown and analyte responses due to laser-material, plasma-material, laser-plasma, plasma-plasma, and laser-laser coupling can be reduced or eliminated.

Embodiments of the invention pertain to a method and apparatus to use a laser pulse to ablate a sample and a second laser pulse to create a plasma to generate atomic emission from the sample. Specific embodiments can be referred to as laser-ablation laser-induced breakdown spectroscopy. Specific embodiments can use two independent laser beams to analyze a sample. The two laser pulses can be provided by a single laser using a beam-splitter or other optics, or by two separate lasers. The first laser pulse samples the material by ablating the sample to create an ablation plume. This laser pulse may or may not create atomic emission. Referring to the embodiment shown in FIG. 1, the ablation plume, which contains the analyte, can then be passed using a carrier gas to a second location to interact with the laser to create the laser-induced analytical plasma. In an alternative embodiment, the ablation plume can be passed to the second plasma via a vacuum, or negative pressure, applied to pull, or draw, the ablation plume to the location of the second laser beam pulse. Such a negative pressure can be produced via, for example, a vacuum pump. The analytical plasma can be formed directly in the carrier gas stream so as to sample the analyte species that were transported in the carrier gas stream. Specific embodiments allow complete decoupling of the ablation event, such as an ablation plasma, from the analytical plasma. Many or all of the non-linearities associated with doing analytical spectroscopy with the analytical plasma formed on or near the sample surface, such as with single LIBS and/or dual-pulse LIBS, can be eliminated. The analytical plasma can be of sufficient energy such that breakdown and plasma formation are essentially independent of the carrier gas stream analyte-loading.

The laser-ablation of the sample can be performed using a variety of laser probes. A pulsed-laser, or other laser setup used to create the laser pulses, can create the ablation plume for transport to the analytical plasma. A laser pulse with pulse-widths in the range of femtoseconds (fs), picoseconds (ps), nanoseconds (ns), or micro-seconds ($\mu$s) can be used. Specific embodiments can have pulse-widths in the range of 1 fs to 10 $\mu$s. The laser pulse can have laser wavelengths in the ultraviolet (UV), Visible, or infrared (IR) ranges. Specific embodiments can use laser pulses having wavelengths in the range from about 193 nm to about 10.6 $\mu$m. A variety of lasers can be used to produce the laser pulse, such as a Nd:YAG laser, an Excimer (ArF, KrF or XeCl) laser, a Ti:Sapphire laser, an Er:YAG, or an Yb:YAG laser. The laser pulses can have energies that range from microJoules to Joules. The laser pulse energy used can be such that a plasma-assisted ablation process occurs, such that a sub-plasma ablation process occurs, such that a laser desorption process occurs, such that a laser-assisted thermal desorption occurs, such that laser-assisted photochemical desorption occurs, and/or a laser-assisted thermal/photochemical desorption process occurs.

The analytical plasma can be created using a variety of set-ups to produce a laser pulse. A pulsed-laser, or other apparatus to produce a laser pulse, can be used to create a laser-induced plasma to serve as an analytical plasma for atomic spectroscopy analysis. Laser pulses with pulse-widths in the femtosecond (fs), picosecond (ps), nanosecond (ns), or micro-second ($\mu$s) range can be used. In specific embodiments, laser pulses with pulse widths in the range of 1 fs-10 us can be used. Laser pulses having wavelengths in the ultraviolet (UV), Visible, or infrared (IR) ranges can be used. Specific embodiments can use laser pulses having wavelengths in the range from about 193 nm to about 10.6 $\mu$m. A variety of lasers can be used to produce the laser pulse, such as a Nd:YAG laser, an Excimer (ArF, KrF or XeCl) laser, a Ti:Sapphire laser, or an Er:YAG laser. Laser pulses can be used having energies from microJoules to Joules, for example, in the range from 50 to 500 milliJoules.

The laser-ablation can be used to sample the material, and the second laser pulse can be used to analyze the material. A carrier gas can be used to transport the ablated sample from the laser ablation location to the analytical laser plasma location. The carrier gas can be, for example, nitrogen, air, helium, argon, krypton or other gas or combinations thereof. Carrier gas flow rates may be adjusted for optimal conditions, and in specific embodiments range from about 1 cc/min to tens of liters/min. The pressure of sample chamber can be at atmospheric pressure or lower or greater than atmospheric pressure.

Analysis of the sample material can involve collecting spectral data from the analytical, or LIBS, plasma. Spectral data can include the ultraviolet, visible, and infrared portions of the electromagnetic spectrum. Spectral data can be collected over times corresponding to the entire plasma lifetime, or to temporal subsets (i.e., selected detector delay and width) with respect to plasma initiation, or combinations thereof. Analysis can further involve producing a metric from the spectral data that corresponds to various atomic emission lines from any species present in the original sample. The metric can be, for example on or more of the following:

1) Total integrated atomic emission peak intensity;
2) The maximum atomic emission peak intensity;
3) The integrated atomic emission, or maximum atomic emission peak intensity, normalized to another atomic emission line or to the adjacent plasma continuum emission or to the total plasma continuum emission, forming a peak-to-base ratio or normalized peak-to-base ratio;
4) The integrated atomic emission, or maximum atomic emission peak intensity, normalized to the adjacent plasma continuum emission noise or to the total plasma continuum emission noise, forming a signal-to-noise ratio; and
5) Ratios of atomic line particular to a specific process of interest.

The spectral data may also be processed by using background subtraction, in which a similar background plasma spectral emission is subtracted from the LIBS spectrum, with the background plasma emission being collected under the same conditions but without the laser-ablation step. Spectral data may be collected for a single analytical, or LIBS, plasma event or for a series of LIBS plasma events, with spectral data processed either individually or averaged together. Spectral data may also be analyzed using any of the available calibration-free LIBS schemes, such as taught in D. Bulajic, M. Corsi, G. Cristoforetti, S. Legnaioli, V. Palleschi, A. Salvetti, E. Tognoni, *Spectrochimica Acta Part B: Atomic Spectroscopy*, 2002, 57, 339-353, which is incorporated by reference herein in its entirety. The resulting metrics from the above desired analysis techniques may be used as absolute analyte signals, or normalized to a single reference element analyte signal or ensemble-average of other reference analyte signals or combinations thereof.

In a specific embodiment, a line-filter can be used on the atomic emission lines in combination with a detector. Embodiments of the subject method can be used to analyze original samples that are a solid, and can also be used to analyze samples that are in the form of a liquid or liquid suspension. Embodiments can use one or two lasers, and can use a variety of laser operating conditions. As examples, the laser-ablation laser and the analytical LIBS laser may be synchronized such that the pulses are fired together; the laser-ablation laser and the analytical LIBS laser may be synchronized such that the pulses are fired with an optimal delay time between the laser pulses; and/or the laser-ablation laser and the analytical LIBS laser may be synchronized with the same repetition rates or asynchronous with different pulse repetition rates, and/or a single laser pulse may be used in combination with a beam-splitter or other optics to divide the beam into two separate laser beams. In a specific embodiment, the analytical LIBS process may involve two analytical laser pulses, with various temporal delays between the two pulses, to achieve what is commonly referred to as dual-pulse LIBS. In a further embodiment, the laser-ablation process may involve two ablation laser pulses, with various temporal delays between the two pulses.

EXAMPLE 1

Seven standard reference materials were investigated, in which 5 elements (Al, Mn, Mg, Fe, and Cu) were analyzed. Four of the standards were from the National Institute of Standards and Technology (NIST), namely NIST-1242 (a cobalt-chromium rich high temperature alloy), NIST-1276a (a cupro-nickel alloy), NIST-1297 (a stainless steel), and NIST-1761 (a low alloy steel). Three samples were cast aluminum standards from Apex Smelting Company (SM-9, SM-10 and S-11). Table 1 gives the certified concentration values, in percentage by mass, for the 5 selected analyte species in all seven standards, as well as other dominant elements present in sample matrix. All the standards were machined into sample coupons (square or round) with a diameter of 2.5 cm and a thickness of 2 to 3 mm.

TABLE 1

Concentration (% by mass) of the five analytical elements present in each certified standard, along with other prominent elements.

| | Concentration (% by mass) | | | | | | |
|---|---|---|---|---|---|---|---|
| | Apex Smelting Co. | | | NIST | | | |
| Element | SM-9 | SM-10 | S-11 | 1242 | 1276a | 1297 | 1761 |
| Al | 85.34 | 84.67 | 89.20 | <0.01 | * | 0.003 | 0.06 |
| Mg | 0.43 | 1.08 | 1.11 | <0.001 | 0.12 | * | * |
| Cu | 3.00 | 2.80 | 0.98 | 0.001 | 67.50 | 0.44 | 0.30 |
| Fe | 3.70 | 1.96 | 0.57 | 1.80 | 0.56 | 69.40 | 95.3 |
| Mn | 0.76 | 0.30 | 0.50 | 1.58 | 1.01 | 7.11 | 0.68 |
| Co | * | * | * | 51.50 | 0.05 | 0.13 | 0.028 |
| Ni | 0.20 | 0.07 | 0.10 | 9.78 | 30.80 | 5.34 | 0.30 |
| Cr | 0.38 | 0.20 | 0.12 | 20.00 | 0.0002 | 16.69 | 0.22 |
| W | * | * | * | 15.10 | * | 0.03 | * |
| Zn | 3.70 | 5.45 | 6.85 | <0.005 | 0.04 | * | * |

* Trace concentrations not reported.

A pulsed laser beam (1064-nm Nd:YAG, 80 mJ/pulse, 10-ns pulse width and 5 Hz repetition rate) was focused on the surface of the target sample using a 100-mm focal length lens. The optics were mounted such that they could be translated, allowing the focal spot to be moved across the sample surface. The laser created a plasma directly on the sample surface, thereby ablating a small crater, and generating a plume of sampled material that moves away from the surface. The sample was mounted in the center of a sealed chamber with optical access via a quartz window that enables the ablation laser to enter. The sample blanks (2.5 cm diameter and 2 to 3 mm thickness) were mounted with adhesive tape to a shaft-mounted disk, which rotated at a constant rate of about 0.25 rev/s and prevented the laser beam from dwelling on the same sample location.

Figure 3:
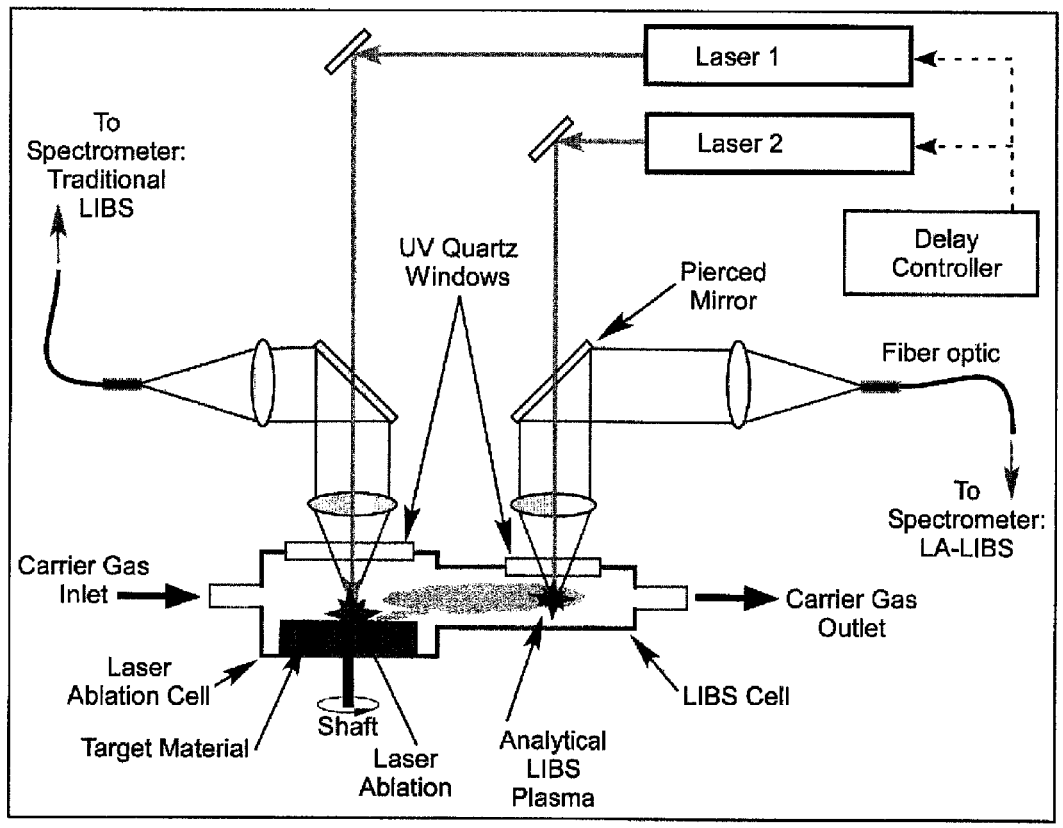
FIG. 3 shows an experimental configuration depicting the traditional LIBS scheme using Laser 1, and the LA-LIBS scheme using Laser 1 for laser ablation, and using Laser 2 for generation of the analytical LIBS plasma in accordance with an embodiment of the subject invention.

FIG. 3 shows the experimental configuration. Plasma emission collection optics were installed to view the resulting, traditional LIBS signal created from the ablation plasma. The plasma emission was collected in backscatter and focused onto a fiber optic bundle which coupled the light into a spectrometer, where the dispersed light was detected by an intensified CCD camera (ICCD) array. The laser ablation LIBS spectroscopy region has a laser-induced plasma created by a focused pulsed laser beam (1064-nm Nd:YAG, 375 mJ/pulse, 10-ns pulse width and 5 Hz repetition rate) directly in the sample stream, on the central axis of the sample chamber, using a 75-mm focal length lens. This laser-induced plasma can be referred to as the analytical plasma or analytical LIBS plasma, created by Laser 2, as shown in FIG. 3. The laser-ablation pulse (Laser 1) was synchronized to the analytical plasma-creating laser pulse (Laser 2) using a delay generator such that the two pulses were fired simultaneously. The nitrogen carrier gas flow rate was adjusted so that the carrier gas would deliver the ablated material directly to the focal spot of Laser 2 at the moment of plasma creation. At steady-state, the analytical plasma samples the ablation plume from preceding laser-ablation pulse or pulses, with the carrier gas flow rate providing the optimal transport of the plume to the focal spot. The atomic emission from the analytical plasma was collected via a backscatter configuration through a UV-grade quartz window, and then collimated by the same focusing lens used to focus the laser beam, then turned by a pierced mirror and focused onto a fiber optic bundle. The emission was then dispersed by a spectrometer and recorded with an ICCD. It is noted that the identical spectrometer and detector were used for all experiments, with the fiber optic location switched for the laser ablation LIBS measurements in accordance with an embodiment of the subject invention and for the traditional LIBS measurements (Laser 1 only). The detector gate widths and delays were adjusted to optimize the analyte emission lines for each experimental configuration and spectral window, between about 1 and 50 µs.

Nitrogen was used as the carrier gas for transporting the ablated material to the laser-induced analytical plasma. The optimal flow rate for the given geometry was determined to be about 3 µm. This provided the best emission signal from the analytical plasma, with no apparent accumulation of ablated material within the laser-ablation sample chamber. The laser-ablation focal spot and the focal spot of the analytical LIBS plasma were located about 10 cm from each other, and connected by a stainless steel tube (I.D.=3.5 cm).

The spectral data was collected using three spectral windows, centered at 250, 275, and 330 nm, using the following procedures. First, measurements were made with the laser ablation LIBS measurement configuration shown in FIG. 3 and described above. The translation stage was set so that the ablation laser was focused approximately halfway between the center and the outer edge of the sample specimen. With the nitrogen carrier gas flowing (3 lpm), both lasers were fired at 5 Hz, and the analyte emission was collected from the analytical plasma (Laser 2) using an average of 600 individual shots, repeated three times, for each of the three spectral windows. In addition, spectra corresponding to an average of 600 shots were collected for each spectral window while blocking the ablation laser (Laser 1) after allowing sufficient time for the sample chamber to be flushed by the carrier gas. These spectra form the background emission of the analytical plasma, and were subsequently used for background subtraction as discussed below. Following each 600-shot average, the translation stage was adjusted, moving the focal spot of the ablation laser toward the sample center with an increment of 500 µm, thereby creating a new ring of ablated craters with every translation step. This procedure was repeated for all seven of the standard reference materials.

Following the laser ablation LIBS data collection, the procedure was repeated for each sample, but with the fiber optic switched such that plasma emission was now collected directly from the ablation plasma (i.e., Laser 1) for identical laser settings and with Laser 2 now shuttered. This configuration represents a traditional, single-laser LIBS experiment for direct sample analysis as a means for comparing the performance to the LA-LIBS embodiment. The translation stage was moved so that the ablation laser was again focused on the outer diameter of the sample disc, but off-set from the previous band of craters. As before, an average of 600 laser shots was collected three times for each spectral window, with the translation stage adjusted so the ablation laser was focused on a fresh region of the metal disc after each 600-shot average. The above procedure was then repeated for each of the seven standards.

Figure 4A:
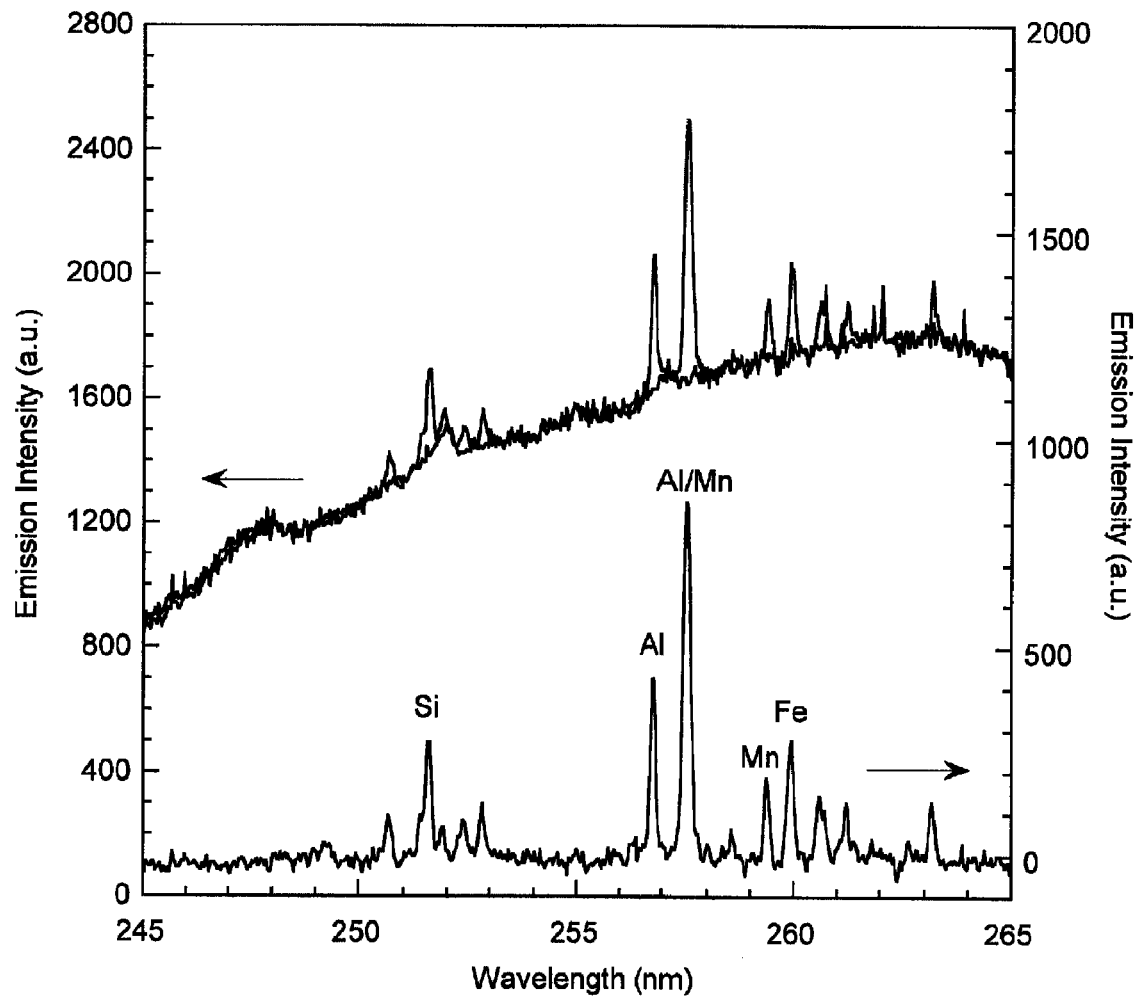
FIG. 4A shows a background subtraction procedure for the 250-nm spectral window for the SM-10 reference material. The upper two spectra correspond to the LA-LIBS emission (spectrum with peaks) and to the background plasma emission collected with no laser ablation. Each spectrum corresponds to a 600-shot average, and both spectra have the same intensity scale (left axis). The lower spectrum is the difference of the two upper spectra (right axis) in accordance with embodiments of the subject invention.

For each analytical emission line of interest, peak-to-base (P/B) calculations were made by summing the full integrated emission line intensity (i.e., full-width) and normalizing to the integrated continuum emission intensity over the same line-width. The P/B ratio represents the atomic emission to continuum emission ratio, which is known to be a robust analytical metric for laser-induced plasmas. For the laser ablation LIBS data taken in accordance with an embodiment of the subject invention, background subtraction was used to readily evaluate the analytical atomic emission peaks and the corresponding continuum emission about the atomic peaks. The usefulness of background subtraction with the laser ablation LIBS approach is depicted in FIG. 4A, noting that the introduction of ablated mass does not affect the overall bulk plasma emission. For the traditional LIBS spectral data, no reference background plasma emission is available, as the plasma emission itself is coupled to each of the individual sample materials. Therefore, the P/B ratios were calculated by dividing the summed absolute emission line intensity by the integrated continuum intensity as determined by averaging the baseline intensity on either side of the atomic emission peak of interest. Table 2 contains the specific atomic emission lines used for analysis, along with the corresponding energy levels.

TABLE 2

Atomic emission lines used for quantitative analysis, along with the related spectroscopic parameters.

| Element | Wavelength (nm) | Transition $(cm^{-1})$ |
|---|---|---|
| Al I | 256.79 | 0-38,929 |
| Mn II | 257.61 | 0-38,807 |
| Mn II | 259.37 | 0-38,543 |
| Mg I | 285.21 | 0-35,051 |
| Mg II | 279.55 | 0-35,761 |
| Cu I | 324.75 | 0-30,784 |
| Cu I | 327.39 | 0-30,535 |
| Fe II | 259.94 | 0-38,459 |

Figure 4B:
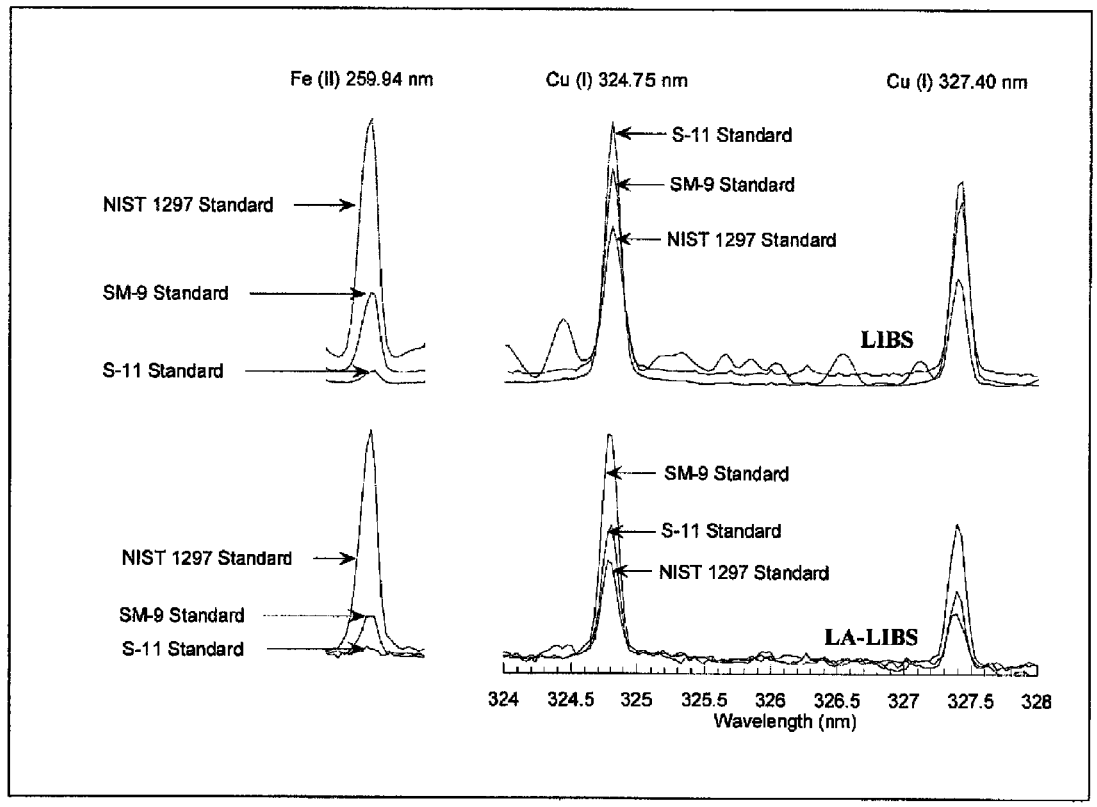
FIG. 4B. shows a spectra depicting the Fe and Cu atomic emission signals for the traditional LIBS data (upper) and for the LA-LIBS data (lower) as recorded for the SM-9, S-11 and NIST-1297 reference materials. Each spectrum corresponds to a single 600-shot average.

To allow a direct comparison of the analytical signals for the different reference materials between the traditional LIBS and laser ablation LIBS data in accordance with an embodiment of the invention, the peak-to-base (P/B) ratios for all the analyte emission lines of interest were calculated and normalized to the P/B ratio of the 259.94-nm Fe II emission line, which was present in the spectra of all standards (see Table 1). FIG. 4B shows the spectra representing emission of the two copper lines for the NIST-1297, SM-9 and S-11 standards, as well as the corresponding Fe II line used to normalize the other analyte emission lines. The spectral data nicely illustrate the inconsistencies due to matrix effects that are present in the traditional LIBS data (i.e., Laser 1 only), but were largely avoided in the laser ablation LIBS data. As observed in FIG. 4B, the Fe line emission intensity ratios scale about equally for both traditional LIBS and laser ablation LIBS spectra for the three reference materials. However, the Cu emission lines are significantly different between the two analytical configurations. In the LIBS spectra, the S-11 standard has a larger Cu signal response than the other two standards, whereas for the laser ablation LIBS data, the SM-9 standard shows the larger Cu response. For the FIG. 4B standards, the actual Cu concentrations are 3.00, 0.98 and 0.442 (% wt.) corresponding to the materials SM-9, S-11 and NIST-1297, respectively. The true Cu concentrations are consistent with the trend present in the laser ablation LIBS spectra, but are not indicative of the trend represented by the traditional LIBS spectra.

Figure 4C:
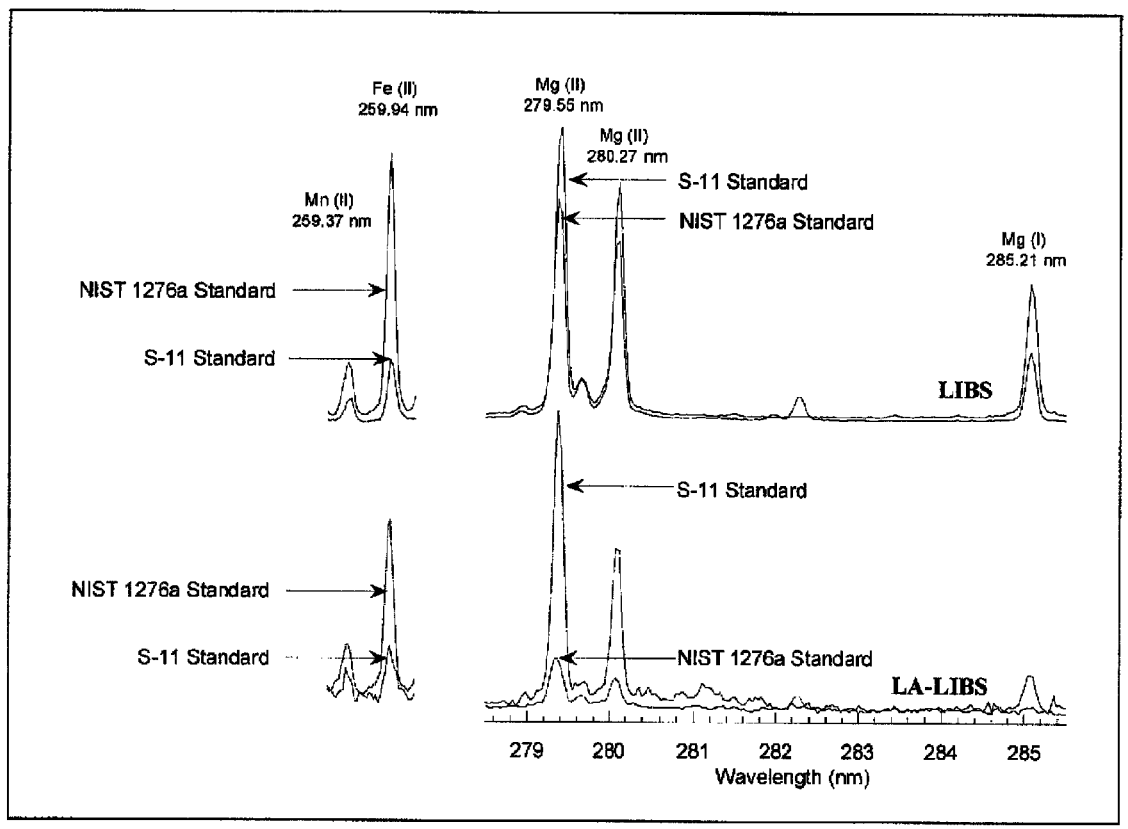
FIG. 4C shows spectra depicting the Fe and Mg atomic emission signals for the traditional LIBS data (upper) and for the LA-LIBS data (lower) as recorded for the S-11 and NIST-1276a reference materials. Each spectrum corresponds to a single 600-shot average.

In a similar manner, FIG. 4C depicts inconsistencies for the Mg analyte emission data for the S-11 and NIST 1276a reference materials. As observed above, the Fe II line intensity ratios are similar when comparing the difference between the two standards for the traditional LIBS and the LA-LIBS spectra. However, the ratios of the Mg line intensities vary considerably between the two data sets. For both techniques, the S-11 standard has the strongest Mg emission intensity, which is as expected given that the true Mg concentration is larger than the NIST-1276a concentration, namely, 1.11% versus 0.12%. The inconsistencies occur when comparing the Mg response of the NIST 1276a. The direct LIBS experiment produced a Mg signal much stronger than expected for the NIST-1276a standard as compared to the S-11 standard in view of the relative Mg concentrations. In contrast, the laser ablation LIBS data reveal a Mg signal for the NIST-1276a standard that is about 10% of the corresponding S-11 Mg emission signal, which is in qualitative agreement with the actual concentration difference. Overall, this trend was consistent with nearly all of the analytical results, in which the laser ablation LIBS configuration provided a more consistent, linear analyte response as compared to the traditional LIBS results.

Figure 5:
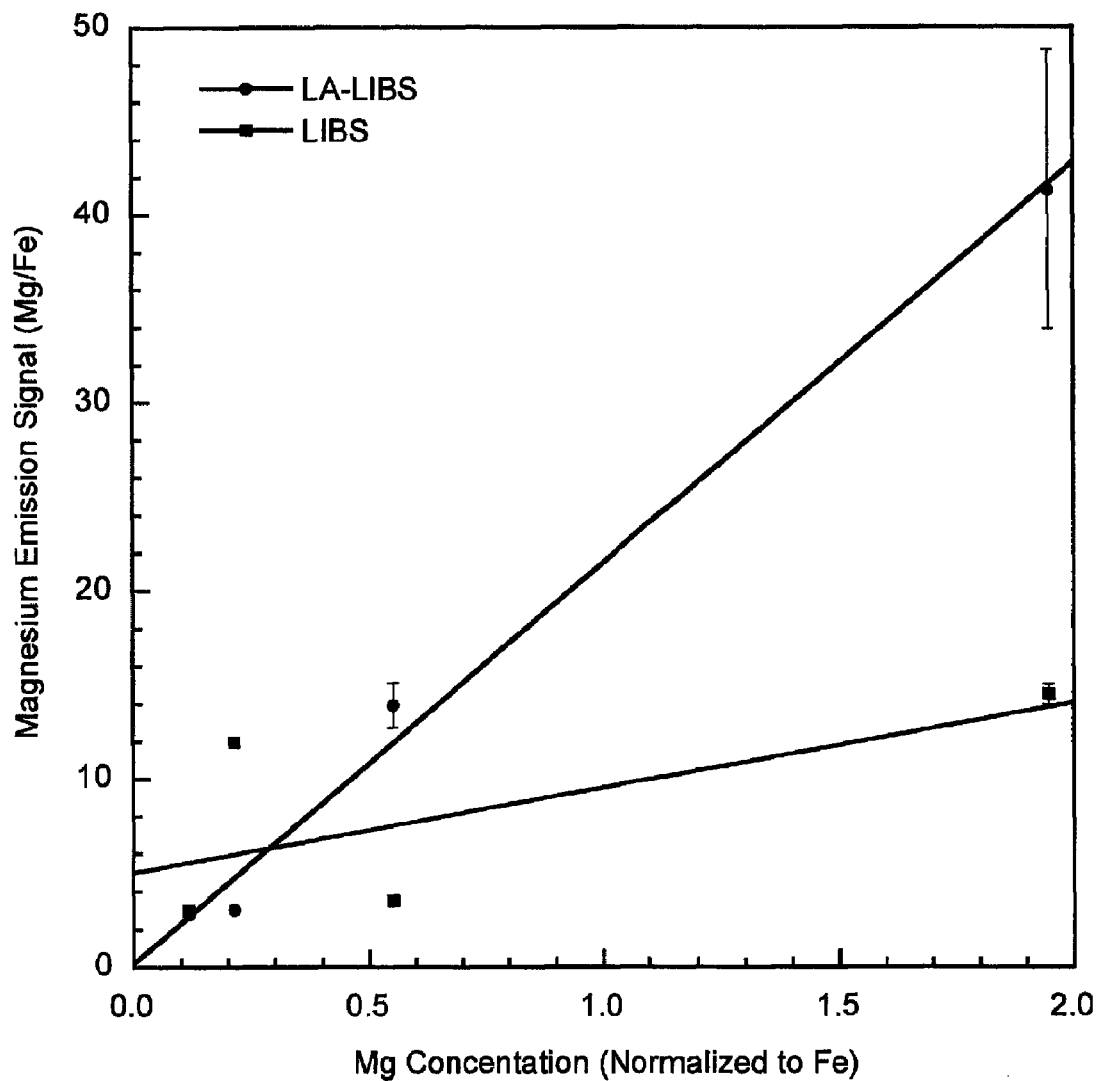
FIG. 5 shows magnesium (279.6-nm Mg II line) calibration curves corresponding to the NIST-1276a, SM-9, SM-10 and S-11 samples for the traditional LIBS and the LA-LIBS data. The actual Mg concentration values are normalized to the actual Fe concentration, and the Mg spectral intensity values are normalized to the Fe spectral intensity values. The lines correspond to a linear least-squares fit and the error bars correspond to the standard deviation of the individual measurements in accordance with embodiments of the subject invention.

To quantify the analytical results for all reference materials, calibration curves were constructed for each analyte present. Since iron was present and observable in every standard, all the data for the other observable emission lines were normalized by the 259.94-nm Fe II emission line. Normalization in this manner provided a means to directly compare the analytical response for the two techniques over the range of reference materials. FIG. 5 presents the calibration curve for the Mg content (279.5-nm Mg II line) for four materials, namely, NIST-1276a, SM-9, SM-10 and S-11. The plots illustrate the increased linearity in calibration when using the laser ablation LIBS technique when compared to the traditional LIBS configuration. The $R^2$ values (0.993 for laser ablation LIBS and 0.433 for LIBS) provide a direct numerical measure of the linearity between the two calibration curves. A complete list of $R^2$ values for each observed analyte emission line is presented in Table 3. Clearly the laser ablation LIBS configuration provides a more linear calibration response over a Mg/Fe range of more than an order of magnitude for the four reference materials. Just as importantly, the laser ablation LIBS calibration curve displays a near zero y-intercept (quantified as 0.46% of the maximum laser ablation LIBS signal response), while the traditional LIBS curve yields a considerable y-intercept value (quantified as 34.5% of maximum LIBS signal response). The rather large relative standard deviation of the laser ablation LIBS highest concentration value (see error bars in FIG. 5) corresponds to the S-11 sample. This sample has one of the lowest iron concentrations, and in fact, has a corresponding Fe emission signal that is near the detection limit, as observed in FIG. 4A, which most likely contributes to the greater variation.

Figure 6:
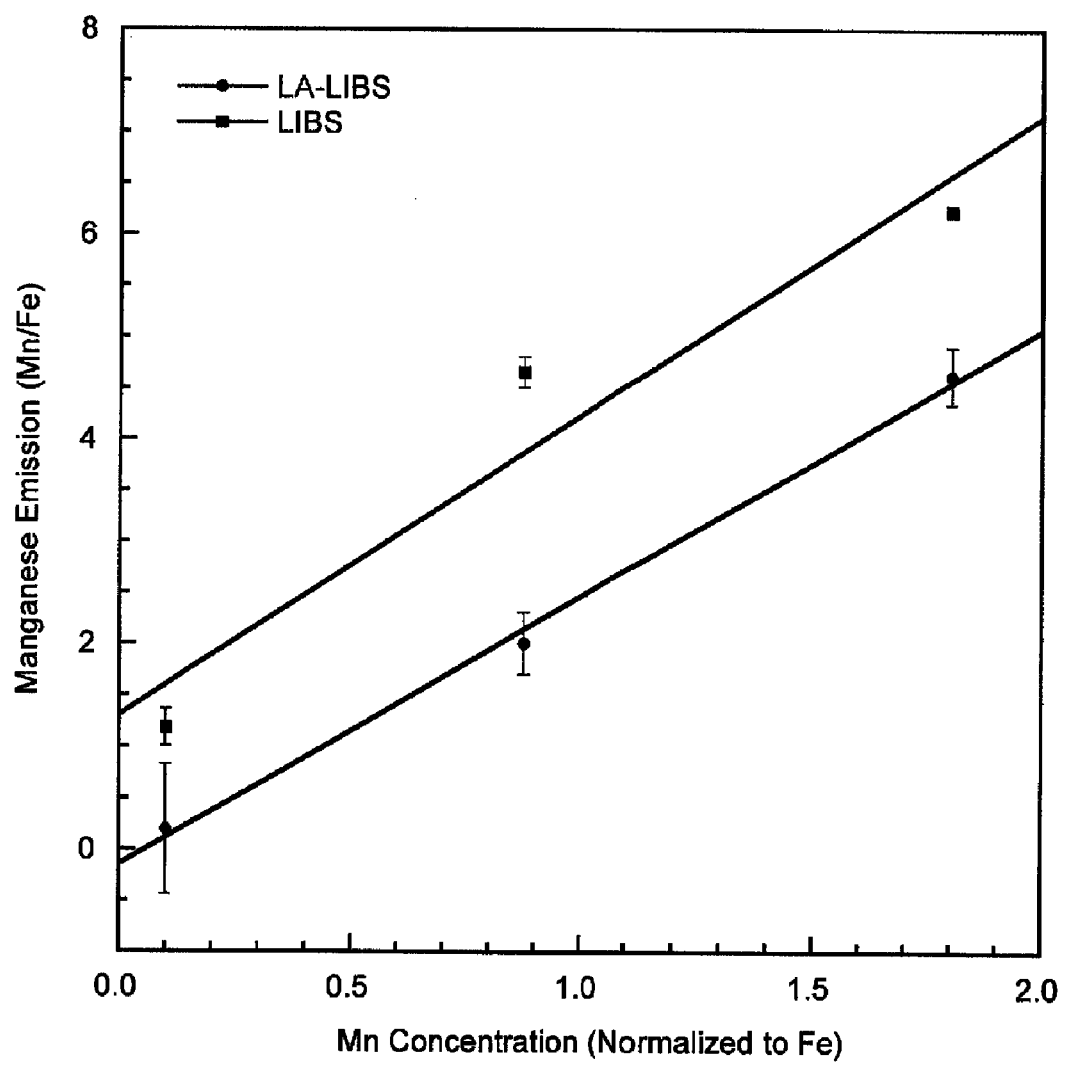
FIG. 6 shows manganese (257.61-nm Mn II line) calibration curves corresponding to the NIST-1276a, NIST-1242 and NIST-1297 samples for the traditional LIBS and the LA-LIBS data. The actual Mn concentration values are normalized to the actual Fe concentration, and the Mn spectral intensity values are normalized to the Fe spectral intensity values. The lines correspond to a linear least-squares fit and the error bars correspond to the standard deviation of the individual measurements in accordance with embodiments of the subject invention.

FIG. 6 presents the calibration curve for the manganese data using 257.6-nm Mn II line for three reference materials, namely, NIST-1276a, NIST-1242 and NIST-1297. As summarized in Table 3, the calibration curve corresponding to the laser ablation LIBS data reveals a larger correlation coefficient and a significantly reduced y-intercept value. It is noted that the spectral data for the three aluminum alloy samples (SM-9, SM-10 and S-11) could not be processed for the 257.61-nm Mn emission line due to spectral interference of the Al I doublet at 257.51 and 257.54 nm, as shown in FIG. 4A. As an alternative, the spectral data were also processed using the 259.37-nm Mn II line for all six reference materials. There appeared to be a spectral irregularities on this line corresponding to the S-11 sample spectra, as present in both the laser ablation LIBS and LIBS data, however, no definitive elemental source could be identified, and the data was therefore included in the final calibration curve. The correlation coefficient of the laser ablation LIBS calibration curve was reduced when including all six samples, while the correlation coefficient of the traditional LIBS curve was slightly improved when including all six samples (see Table 3). For both of the Mn emission lines, the y-intercept value of the laser ablation LIBS calibration curves was significantly improved as compared to the LIBS calibration curves.

Overall, the laser ablation LIBS configuration revealed a significantly greater correlation coefficient as compared to the traditional LIBS analysis when considering all the calibration curve data in Table 3, with an average $R^2$ value of 0.953 as compared to 0.779. Equally important, the laser ablation LIBS analysis revealed a y-intercept value much closer to zero than the calibration curves realized with the LIBS analysis, with an average offset value (as based on absolute values of the percent deviations) equal to 2.4% of the maximum analytical values, as compared to an average y-intercept offset of 15.5% of the maximum analytical values for the traditional LIBS data. When considering all of the calibration curves, the laser ablation LIBS parameters (i.e., $R^2$ and y-intercept values) were superior to the traditional LIBS parameters in all cases except for the single $R^2$ value corresponding to the Mn calibration data using the 259.37-nm emission line. As noted above, this data set was significantly influenced by the S-11 data point, which when removed increased the $R^2$ values to 0.93 and 0.99 for the laser ablation LIBS and LIBS calibration curves, respectively.

Given the significant improvements in the analytical performance of the laser ablation LIBS, or LA-LIBS, configuration as compared to the traditional, single-pulse LIBS, it is useful to explore the analytical sample as presented to the LIBS plasma of the LA-LIBS configuration. Several items are readily suggested for discussion, including the particle size distribution as transported from the laser-ablation plume through the sample chamber to the analytical LIBS plasma, and the resulting analyte concentration at this sample point. Regarding the particle size distribution, a robust analytical response would require a high degree of particle vaporization by the analytical LA-LIBS plasma. Several studies have reported the effect of particle size on the analyte response for LIBS-based aerosol analysis. Carranza and Hahn reported an upper size limit of 2.1-µm for complete particle vaporization of silica microspheres using a laser pulse energy of 320 mJ, for an experimental configuration similar to the current study (J. E. Carranza, D. W. Hahn, *Analytical Chemistry*, 2002, 74, 5450-5454.). A more recent study examined the complete vaporization of carbon-rich particles (specifically glucose particles and sodium hydrogenocarbonate particles) in a laser-induced plasma, and reported an upper size limit of 5 µm

TABLE 3

List of the calculated $R^2$ values and y-intercept values for the traditional LIBS and laser ablation LIBS calibration curves constructed for each observed emission line. The intensity of the analyte was normalized by the intensity of the Fe (II) 259.94 nm line. The y-intercept values is presented as a percentage of the maximum analyte signal for each respective calibration curve.

| Element | Wavelength (nm) | LA-LIBS $R^2$ | y-Intercept | Traditional LIBS $R^2$ | y-Intercept |
|---|---|---|---|---|---|
| Al I | 256.8 | 0.995 | 1.2% | 0.982 | 19.5% |
| Mn II | 257.6 | 0.997 | −3.2% | 0.931 | 21.1% |
| Mn II | 259.4 | 0.794 | 5.6% | 0.953 | 12.8% |
| Mg I | 285.2 | 0.999 | 0.39% | 0.928 | 9.0% |
| Mg II | 279.6 | 0.993 | 0.46% | 0.433 | 34.5% |
| Cu I | 324.8 | 0.971 | −5.5% | 0.618 | −5.9% |
| Cu I | 327.4 | 0.920 | −0.27% | 0.611 | −6.0% |
| Average | | 0.953 | 2.4% | 0.779 | 15.5% | for complete vaporization (E. Vors, L. Salmon, *Analy. Bioanaly. Chem.*, 2006, 385, 281-286).

Figure 7:
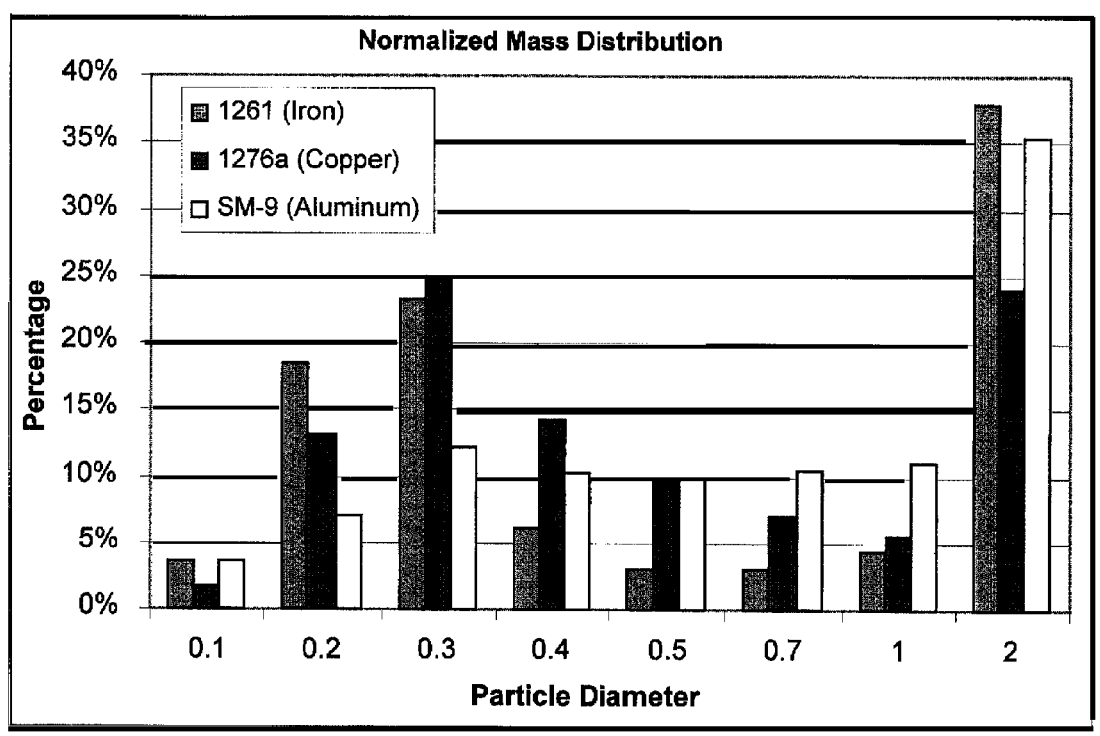
FIG. 7 shows a normalized mass distribution as a function of particle diameter corresponding to ablation of the NIST-1761, NIST-1276a and SM-9 reference materials.

The results of the particle sizing measurements are presented in FIG. 7, where the normalized mass distribution is presented for three of the reference materials, namely, NIST-1761, NIST-1276a and SM-9. While the data appears to be bi-modal in nature, it is noted that the largest size bin (2-µm) corresponds to all particles with a size greater than or equal to 2 µm. Therefore, if additional resolution was provided for the larger particles sizes, the mass distribution would be expected to monotonically decrease with size. Several comments are offered. The majority of particles as transported to the analytical plasma are in the sub-micron size regime, and therefore, complete particle vaporization is expected for this size range. It is also estimated that the majority of the particles greater than 2 µm (which represents about 25 to 35% of ablated mass) will fall in the 2 to 5 µm range, and therefore, within the range of sizes also expected for complete or near-complete vaporization, as based on the above comments. An advantage of LA-LIBS can be the complete uncoupling of the laser-ablation and analytical plasma stages. In specific embodiments, laser-ablation can be accomplished with deeper UV lasers (e.g. 193-nm excimer or 355-nm Nd:YAG).

Figure 8:
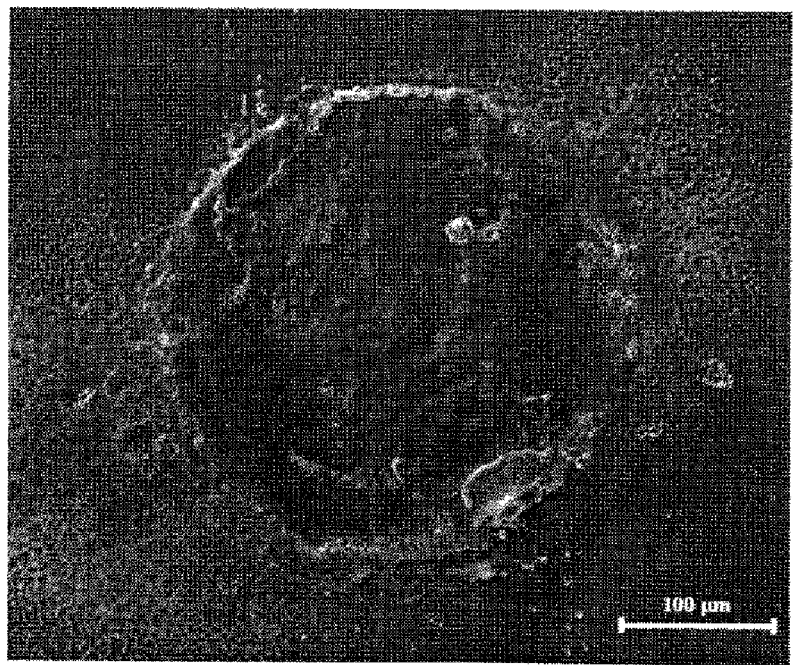
FIG. 8 shows SEM images of the ablation craters after 10 laser pulses for the NIST-1761 (top) and NIST-1276a (bottom) reference materials.
Figure 8:
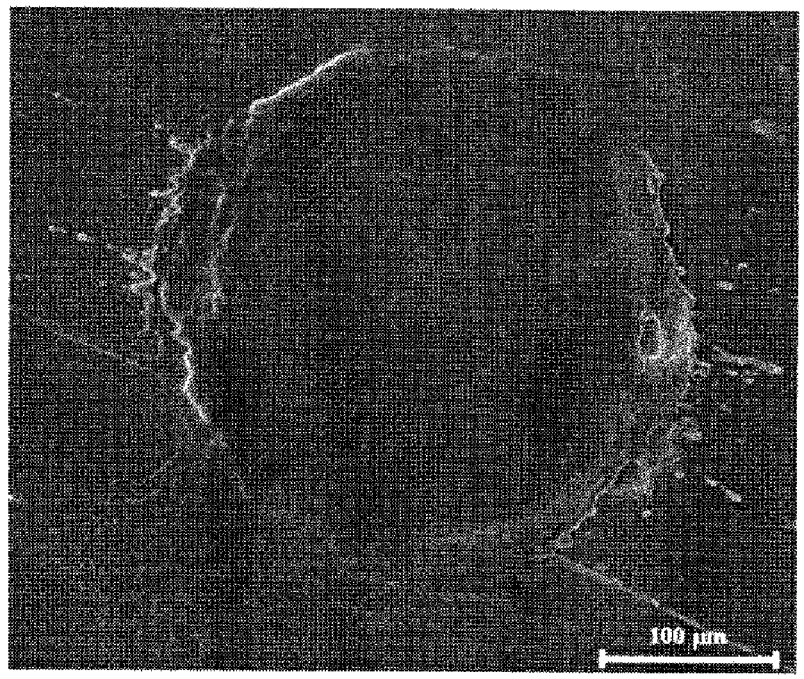

An important issue with the LA-LIBS configuration is the transport of analyte from the laser-ablation step and the subsequent delivery to the analytical LIBS plasma. Sample dilution may occur as the laser-ablation plume is transported by the carrier gas, undergoing plume expansion and particle diffusion during the process. It is useful to estimate the sample concentration as presented to the analytical LIBS plasma following transport. First, an estimate of the ablated mass was accomplished by analyzing the individual ablation craters with a white-light interferometer, allowing depth profiles to be measured from which a volume of ablated material was estimated. This process was done for craters corresponding to 1, 5, 10 or 20 laser shots as a means to enhance the precision of the crater measurements by deepening the crater depth with multiple laser shots. The resulting crater mass was then divided by the respective number of laser shots, to produce the average ablated mass per laser shot. The measured crater diameters and mass ablation rates for each of the three standards analyzed (SM-9, NIST-1761 and NIST 1276a) are summarized in Table 4, noting that these standards correspond to the same standards used for the particle size measurements. As observed in Table 4, these three representative reference materials all yielded similar ablation parameters, namely, a crater diameter of about 260 µm and an ablated mass of about 13-14 ng. In addition to the white-light interferometry analysis, SEM images were recorded for the same material samples, as shown in FIG. 8. The craters are typical of laser ablation with infrared, Q-switched lasers, revealing a raised crater rim and signs of splashing around the perimeter of the craters, both characteristic of sample melting processes.

TABLE 4

Data representing the average crater size and ablation rates for the SM-9, NIST-1761 and NIST 1276a) reference standards.

|  | SM-9 | NIST-1761 | NIST-1276a |
|---|---|---|---|
| Crater Diameter (µm) | 250 | 270 | 260 |
| Mass/Pulse (ng) | 13 | 13 | 14 |

Using the Table 4 parameters, a rough estimate of the analyte mass concentration in the vicinity of the analytical plasma focal spot can be made. Based on the analyte response as a function of carrier gas velocity, the core of the ablation plume was estimated to fall within a spatial region of about 1.5 cm in diameter at the location of the analytical plasma. Using the corresponding volume and ablated mass, the total mass concentration at the analytical LIBS plasma is estimated as 7,400 µg/m$^3$. For constituent elements on the order of 1% weight by mass, which is consistent with many of the elements examined in the current study, the analyte mass concentration would be on the order of 70 µg/m$^3$. This value is comparable to detection limits reported for many metals with the aerosol LIBS methodology (B. T. Fisher, H. A. Johnsen, S. G. Buckley, D. W. Hahn, *Applied Spectroscopy*, 2001, 55, 1312-1319), and consistent with the previous comments about the iron concentration of S-11 nearing the detection limit. It is not surprising that the current implementation of the LA-LIBS configuration may be signal limited for some analyte species at concentrations approaching the 1% level. As implemented, the plume expansion at the sample point is diluted by many orders of magnitude as compared to the mass concentration within the original ablation plasma. However, as discussed above, the current geometry is by no means optimized with respect to particle transport. For example, the relatively long transport distance of 10 cm used in the current study could be reduced. One can envision a carefully optimized system in which the analyte concentration as delivered to the analytical plasma is increased by an order of magnitude or more.

With regard to the analyte signals, the spectral data were also analyzed to calculate the signal-to-noise ratio (SNR), which may be considered a better analytical figure of merit than the P/B ratio. For all elements over the range of reference samples, the ratio of the SNR value of the LIBS analysis to the corresponding SNR value of the LA-LIBS data ranged from 1.2 to nearly 13, with an average ratio of 5.2. Therefore, on average, the SNR value of a given element for a given reference sample was about 5 times larger for the traditional LIBS emission as compared to the LA-LIBS data. This result shows an advantage with respect to the LA-LIBS approach, as a reduction in signal-to-noise ratio by only a factor of 5 is considered a positive result given the considerable sample dilution with the current configuration. The signal-to-noise ratio can be improved with the LA-LIBS approach due to the independent, gas-breakdown initiated analytical plasma, which is very repeatable with regard to the LIBS method in general, and conducive to background subtraction, both of which contribute to the analytical figure of merit.

EXAMPLE 2

Figure 9:
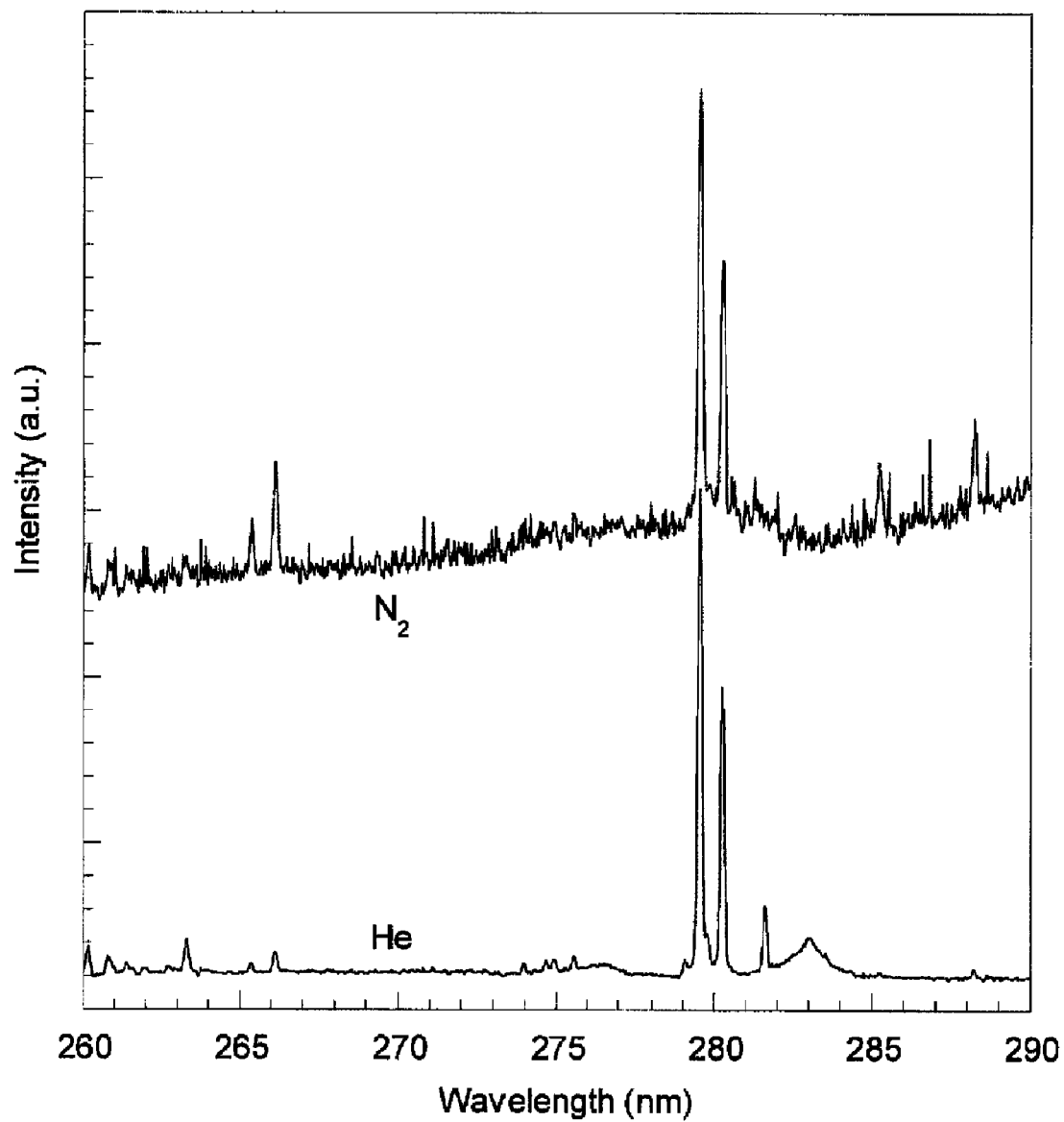
FIG. 9 shows an LA-LIBS spectra as recorded using a nitrogen carrier gas (upper) and a helium carrier gas (lower)

The effects of carrier gas were examined using the same experimental conditions for Example 1 for the SM-10 reference sample. The laser ablation LIBS measurements were repeated for a pristine SM-10 sample using the identical experimental methodology, but with the nitrogen carrier gas replaced with a carrier gas flow of pure helium at a rate of 1.5 lpm. While no detailed optimization was performed, a better analyte response was observed for the helium carrier gas, as compared to the nitrogen carrier gas. FIG. 9 presents representative spectra for the laser ablation LIBS measurements as recorded in nitrogen and helium carrier gases. Examination of the two spectra reveals a reduction in spectral noise with the change to helium. The signal-to-noise ratio (SNR) was used to assess the improvements in analytical performance with helium. The signal-to-noise values were calculated by taking the ratio of the full-peak area to the rms-noise, as measured from the adjacent continuum emission. Table 2 contains the specific atomic emission lines used for analysis, along with the corresponding energy levels. For the five elements examined in this study, the SNR values were found to increase by an average factor of 7.2 when changing from a nitrogen to helium carrier gas.

EXAMPLE 3

The effects of carrier gas flow rate were examined using experimental conditions similar to Example 1, but with the following changes. The laser ablation event was performed with a frequency-tripled Nd:YAG laser at 355-nm wavelength and pulse energy of 40 mJ/pulse. The analytical laser-induced plasma was created using a fundamental Nd:YAG laser at 1064-nm wavelength and pulse energy of 200 mJ/pulse. The ablation cell was of diameter about 1⅜" with a height (target to quartz window) of about 0.9". An inlet of about 3/16" diameter allowed carrier gas to enter the ablation cell and an diametrically opposed outlet of about 3/16" diameter allowed the carrier gas and ablation plume to exit the ablation cell. The exit was directly coupled to an adjoining laser-induced plasma cell by a single tube about 2" long and about 3/16" diameter. The tube exited directly at the focal spot of the analytical laser-induced plasma, which sampled the ablation plume. The two laser pulses were synchronized at 5 Hz, and approximately aligned temporally. Under these conditions, the ablation plume is transported by the carrier gas to the analytical LIBS plasma in about 200 milliseconds. This allows the plume to arrive at the center of the analytical LIBS plasma in time for analysis by the next laser pulse. Because the analytical LIBS plasma is analyzing the ablation plume from the previous ablation laser pulse, there is complete uncoupling of the ablation event and the analytical plasma event. It is expected that an optimal carrier gas flow rate exists to deliver the ablation plume at the appropriate time and thereby produce a maximum atomic emission signal. A pure copper target was used as the ablation target and copper atomic emission signals at 324.7 and 327.4 nm were analyzed. FIG. 10 shows the copper atomic emission signal as a function of the carrier gas flow rate for this example. The data demonstrate that the plume is successfully transported to the analytical LIBS plasma by the carrier gas, to achieve uncoupled laser ablation and analytical laser-induced plasma spectroscopy.

In an embodiment, one or more of steps of the various embodiments of the subject method described herein are performed by one or more suitably programmed computers. In a particular embodiment, analyzing the collected atomic emission is performed by the one or more suitably programmed computers. Computer-executable instructions for analyzing the collected atomic emission can be embodied on one or more computer-readable media as described below. In an embodiment, the one or more suitably programmed computers incorporate a processing system as described below. In an embodiment, the processing system is part of a system for implementing the control of the laser beam pulses and transport of the ablation plume.

In an embodiment, computer-executable instructions for providing an interface can be embodied on one or more computer-readable media as described below. In an embodiment, the interface can be presented on one or more suitably programmed computers. In an embodiment, the one or more suitably programmed computers incorporate a processing system as described below. In an embodiment, one or more components of a data structure for the various embodiments of the subject method are embodied on one or more computer-readable media as described below. In an embodiment, the data structure can be accessed via one or more suitably programmed computers. In an embodiment, the one or more suitably programmed computers incorporate a processing system as described below. Aspects of the invention can be described in the general context of computer-executable instructions, such as program modules, being executed by a computer. Generally, program modules include routines, programs, objects, components, data structures, etc., that perform particular tasks or implement particular abstract data types. Such program modules can be implemented with hardware components, software components, or a combination thereof. Moreover, those skilled in the art will appreciate that the invention can be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, formats, and numerous other details including operating environments and the like are set forth to provide a thorough understanding of the present invention. In other instances, structures, devices, and processes are shown in block-diagram form, rather than in detail, to avoid obscuring the present invention. But an ordinary-skilled artisan would understand that the present invention can be practiced without these specific details. Computer systems, servers, work stations, and other machines can be connected to one another across a communication medium including, for example, a network or networks.

As one skilled in the art will appreciate, embodiments of the present invention can be embodied as, among other things: a method, system, or computer-program product. Accordingly, the embodiments can take the form of a hardware embodiment, a software embodiment, or an embodiment combining software and hardware. In an embodiment, the present invention takes the form of a computer-program product that includes computer-useable instructions embodied on one or more computer-readable media. Methods, data structures, interfaces, and other aspects of the invention described above can be embodied in such a computer-program product.

Computer-readable media include both volatile and nonvolatile media, removable and nonremovable media, and contemplate media readable by a database, a switch, and various other network devices. By way of example, and not limitation, computer-readable media incorporate media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently. In an embodiment, non-transitory media are used.

The invention can be practiced in distributed-computing environments where tasks are performed by remote-processing devices that are linked through a communications network or other communication medium. In a distributed-computing environment, program modules can be located in both local and remote computer-storage media including memory storage devices. The computer-useable instructions form an interface to allow a computer to react according to a source of input. The instructions cooperate with other code segments or modules to initiate a variety of tasks in response to data received in conjunction with the source of the received data.

The present invention can be practiced in a network environment such as a communications network. Such networks are widely used to connect various types of network elements, such as routers, servers, gateways, and so forth. Further, the invention can be practiced in a multi-network environment having various, connected public and/or private networks.

Communication between network elements can be wireless or wireline (wired). As will be appreciated by those skilled in the art, communication networks can take several different forms and can use several different communication protocols.

Embodiments of the subject invention can be embodied in a processing system. Components of the processing system can be housed on a single computer or distributed across a network as is known in the art. In an embodiment, components of the processing system are distributed on computer-readable media. In an embodiment, a user can access the processing system via a client device. In an embodiment, some of the functions or the processing system can be stored and/or executed on such a device. Such devices can take any of a variety of forms. By way of example, a client device may be a desktop, laptop, or tablet computer, a personal digital assistant (PDA), an MP3 player, a communication device such as a telephone, pager, email reader, or text messaging device, or any combination of these or other devices. In an embodiment, a client device can connect to the processing system via a network. As discussed above, the client device may communicate with the network using various access technologies, both wireless and wireline. Moreover, the client device may include one or more input and output interfaces that support user access to the processing system. Such user interfaces can further include various input and output devices which facilitate entry of information by the user or presentation of information to the user. Such input and output devices can include, but are not limited to, a mouse, touchpad, touch-screen, or other pointing device, a keyboard, a camera, a monitor, a microphone, a speaker, a printer, a scanner, among other such devices. As further discussed above, the client devices can support various styles and types of client applications.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. An apparatus for producing atomic emission, comprising:
   a target holder, wherein the target holder is adapted to hold a target, wherein the target comprises target material;
   at least one laser, wherein the at least one laser is configured to generate a first laser beam pulse, wherein the first laser beam pulse is directed to the target to create an ablation event so as to produce an ablation plume of target material; and
   a transport system, wherein the transport system transports at least a portion of the ablation plume of target material a distance d from the ablation event, wherein the at least one laser is configured to generate a second laser beam pulse, wherein the second laser beam pulse is directed to the at least a portion of the ablation plume of target material transported a distance d from the ablation event to produce an analytical plasma, such that one or more elements of the at least a portion of the ablation plume of target material undergo atomic emission, wherein d is sufficiently large that the analytical plasma is uncoupled from the ablation event, wherein the transportation system comprises a flowing carrier gas.

2. The apparatus according to claim 1, wherein the ablation event is a plasma ablation event.

3. The apparatus according to claim 1, wherein the ablation event is a sub-plasma ablation event.

4. The apparatus according to claim 1, wherein the ablation event is selected from the group consisting of: a thermal desorption ablation event, a laser desorption event, a laser-assisted desorption event, a laser-assisted photochemical desorption event, and a laser-assisted thermal/photochemical desorption event.

5. The apparatus according to claim 1, further comprising:
   a collection system, wherein the collection system collects at least a portion of the atomic emission from the one or more elements of the at least a portion of the ablation plume of target material.

6. The apparatus according to claim 5, further comprising:
   an analyzer system, wherein the analyzer system analyzes the collected atomic emission to determine information regarding the target material.

7. The apparatus according to claim 1, wherein the at least one laser is a first laser.

8. The apparatus according to claim 7, further comprising a beam splitter, wherein the beam splitter splits a first pulsed laser beam from the first laser so as to produce the first laser beam pulse and the second laser beam pulse.

9. The apparatus according to claim 1, wherein the at least one laser comprises a first laser configured to generate the first laser beam pulse and a second laser configured to generate the second laser beam pulse.

10. The apparatus according to claim 1, wherein d is in the range 0.5 cm to 2 m.

11. The apparatus according to claim 1, wherein d is in the range 1 cm to 10 cm.

12. The apparatus according to claim 1, wherein d is in the range 2 cm to 6 cm.

13. The apparatus according to claim 1, further comprising:
   a first focusing lens configured to focus the first laser beam pulse onto the target material to create the ablation event; and
   a second focusing lens configured to focus the second laser beam onto the at least a portion of the ablation plume of target material transported a distance d from the ablation event to produce the analytical plasma.

14. The apparatus according to claim 1, wherein a negative pressure gradient causes the carrier gas to flow.

15. The apparatus according to claim 1, wherein a positive pressure gradient causes the carrier gas to flow.

16. The apparatus according to claim 1, wherein the second laser beam pulse produces the analytical plasma a time period after the first laser beam pulse produces the ablation event, wherein the time period is an amount of time to transport the at least a portion of the ablation plume a distance d from the ablation event.

17. The apparatus according to claim 9, further comprising a delay controller, wherein the delay controller is configured to cause the generation of the first laser beam pulse and cause the generation of the second laser beam pulse a delay period after the generation of the first laser beam pulse.

18. The apparatus according to claim 6, wherein the analyzer system comprises a spectrometer.

19. The apparatus according to claim 18, wherein the analyzer system further comprises a detector.

20. The apparatus according to claim 6, wherein the analyzer system comprises a line-filter.

21. The apparatus according to claim 20, wherein the analyzer system further comprises a detector.

22. A method for producing atomic emission, comprising:
  directing a first laser beam pulse to a target wherein the target comprises a target material, to produce an ablation event such that an ablation plume of target material is produced;
  transporting at least a portion of the ablation plume of target material a distance d away from the ablation event, wherein transporting at least a portion of the ablation plume of target material a distance d away from the ablation event comprises transporting the at least a portion of the ablation plume of target material via a flowing carrier gas; and
  directing a second laser beam pulse to the at least a portion of the ablation plume of target material transported a distance d from the ablation event to produce an analytical plasma such that one or more elements of the at least a portion of the ablation plume of target material undergo atomic emission, wherein d is sufficiently large that the analytical plasma is uncoupled from the ablation event.

23. The method according to claim 22, wherein the ablation event is a plasma ablation event.

24. The method according to claim 22, wherein the ablation event is a sub-plasma ablation event.

25. The method according to claim 22, wherein the ablation event is selected from the group consisting of: a thermal desorption ablation event, a laser desorption event, a laser-assisted desorption event, a laser-assisted photochemical desorption event, and a laser-assisted thermal/photochemical desorption event.

26. The method according to claim 22, further comprising:
  collecting the atomic emission from the one or more elements of the at least a portion of the ablation plume of target material.

27. The method according to claim 26, further comprising:
  analyzing the collected atomic emission to determine information regarding the target material.

28. The method according to claim 22, wherein the first laser beam pulse and the second laser beam pulse are generated by a first laser.

29. The method according to claim 28, further comprising splitting a first pulsed laser beam from the first laser so as to produce the first laser beam pulse and the second laser beam pulse.

30. The method according to claim 22, wherein the first laser beam pulse is generated by a first laser and the second laser beam pulse is generated by a second laser.

31. The method according to claim 22, wherein d is in the range 0.5 cm to 2 m.

32. The method according to claim 22, wherein d is in the range 1 cm to 10 cm.

33. The method according to claim 22, wherein d is in the range 2 cm to 6 cm.

34. The method according to claim 22, further comprising:
  focusing the first laser beam pulse onto the target material via a first focusing lens to create the ablation event; and
  focusing the second laser beam onto the at least a portion of the ablation plume of target material transported a distance d from the ablation event via a second focusing lens to produce the analytical plasma.

35. The method according to claim 22, wherein a positive pressure gradient causes the carrier gas to flow.

36. The method according to claim 22, wherein a negative pressure gradient causes the carrier gas to flow.

37. The method according to claim 22, wherein the second laser beam pulse produces the analytical plasma a time period after the first laser beam pulse produces the ablation event, wherein the time period is an amount of time to transport the at least a portion of the ablation plume a distance d from the ablation event.

38. The method according to claim 30, further comprising generating the first laser beam pulse and generating the second laser beam pulse a delay period after generating the first laser beam pulse.

39. The method according to claim 27, wherein analyzing the collected atomic emission comprises analyzing the collected atomic emission via a spectrometer and a detector.

40. The method according to claim 27, wherein analyzing the collected atomic emission comprises analyzing the collected atomic emission via a line-filter and a detector.

* * * * *

UNITED STATES PATENT AND TRADEMARK OFFICE
CERTIFICATE OF CORRECTION

Page 1 of 2

PATENT NO. : 8,319,964 B2
APPLICATION NO. : 13/382825
DATED : November 27, 2012
INVENTOR(S) : David Worthington Hahn It is certified that error appears in the above-identified patent and that said Letters Patent is hereby corrected as shown below:

In the Specification:

Column 3,
Line 66, "analytical current single-laser" should read
--analytical LIBS plasma. Embodiments of the subject method can offer significant advantages over current single-laser--.

Column 6,
Line 43, "range of 1 fs-10 us" should read --range of 1 fs – 10 μs--.

Column 9,
Line 22, "about 3 μm" should read --about 3 lpm--.

In the Claims:

Column 17,
Line 65, "a distance d" should read --a distance $d$--.

Column 18,
Line 2, "a distance d" should read --a distance $d$--.
Line 5, "wherein d" should read --a distance $d$--.
Line 38, "wherein d" should read --wherein $d$--.
Line 40, "wherein d" should read --wherein $d$--.
Line 42, "wherein d" should read --wherein $d$--.
Line 51, "a distance d" should read --a distance $d$--.
Line 61, "a distance d" should read --a distance $d$--.

Signed and Sealed this
First Day of July, 2014

Michelle K. Lee
*Deputy Director of the United States Patent and Trademark Office*

Column 19,
Line 15, "a distance d" should read --a distance $d$--.
Line 17, "a distance d" should read --a distance $d$--.
Lines 22-23, "a distance d" should read --a distance $d$--.
Line 26, "wherein d" should read --wherein $d$--.

Column 20,
Line 11, "wherein" should read --a distance $d$--.
Line 13, "wherein" should read --a distance $d$--.
Line 15, "wherein" should read --a distance $d$--.
Lines 21-22, "a distance d" should read --a distance $d$--.
Line 32, "a distance d" should read --a distance $d$--.